US009488557B2

(12) United States Patent
Lancaster, III et al.

(10) Patent No.: US 9,488,557 B2
(45) Date of Patent: Nov. 8, 2016

(54) MACHINE GENERATED WRAP DATA (71) Applicant: Lantech.com, LLC, Louisville, KY (US)

(72) Inventors: Patrick R. Lancaster, III, Louisville, KY (US); Michael Mitchell, Louisville, KY (US); Thomas Harris, Louisville, KY (US); Robert D. Janes, Sr., Louisville, KY (US); Richard L. Johnson, La Grange, KY (US)

(73) Assignee: Lantech.com, LLC, Louisville, KY (US)

( * ) Notice: Subject to any disclaimer, the term of this patent is extended or adjusted under 35 U.S.C. 154(b) by 0 days.

(21) Appl. No.: 14/808,751

(22) Filed: Jul. 24, 2015

(65) Prior Publication Data

US 2015/0353220 A1 Dec. 10, 2015

Related U.S. Application Data (63) Continuation-in-part of application No. 13/284,528, filed on Oct. 28, 2011, which is a continuation of application No. 13/623,500, filed on Sep. 20, 2012, now abandoned.

(60) Provisional application No. 61/408,543, filed on Oct. 29, 2010, provisional application No. 61/538,373, filed on Sep. 23, 2011.

(51) Int. Cl.
*B65B 11/00* (2006.01)
*G01N 3/02* (2006.01)
(Continued)

(52) U.S. Cl.
CPC ............... *G01N 3/02* (2013.01); *B65B 11/025* (2013.01); *B65B 11/045* (2013.01); *B65B 57/00* (2013.01); *B65B 57/18* (2013.01);
(Continued)

(58) Field of Classification Search
CPC ..... B65B 11/00; B65B 11/08; B65B 11/045; B65B 2011/002
USPC .......................................................... 53/461
See application file for complete search history.

(56) References Cited

U.S. PATENT DOCUMENTS 3,815,313 A * 6/1974 Heisler .................. B65B 9/026
206/497
3,867,806 A 2/1975 Lancaster, III et al.
(Continued)

FOREIGN PATENT DOCUMENTS

WO 2007100596 A2 9/2007
WO 2012058596 A1 5/2012

OTHER PUBLICATIONS

European Patent Office; Search Report and Written Opinion in International Patent Application No. PCT/US2011/058393 dated Feb. 14, 2012; 9 pages.
(Continued)

*Primary Examiner* — Andrew M Tecco
*Assistant Examiner* — Chelsea Stinson
(74) *Attorney, Agent, or Firm* — Middleton Reutlinger (57) ABSTRACT Various methods are provided for determining and displaying wrapping data generated by a wrapping machine during wrapping of a load with a packaging material, e.g., to determine numbers of layers of packaging material applied to a load, a containment force applied to a load, and/or whether a load meets a predetermined minimum required containment force standard for the load.

47 Claims, 5 Drawing Sheets (51) Int. Cl.
*B65B 57/18* (2006.01)
*B65B 11/02* (2006.01)
*B65B 11/04* (2006.01)
*B65B 57/00* (2006.01)

(52) U.S. Cl.
CPC ..... *B65B 2011/002* (2013.01); *B65B 2210/18* (2013.01); *B65B 2210/20* (2013.01)

(56) References Cited

U.S. PATENT DOCUMENTS

| | | | |
|---|---|---|---|
| 4,077,179 | A | 3/1978 | Lancaster et al. |
| 4,501,105 | A | 2/1985 | Rogers et al. |
| 4,514,955 | A | 5/1985 | Mouser et al. |
| 4,545,182 | A | 10/1985 | McDowell, Jr. |
| 5,369,416 | A | 11/1994 | Haverty et al. |
| 6,370,839 | B1 * | 4/2002 | Nakagawa ............ B65B 11/008 52/211 |
| 7,114,308 | B2 * | 10/2006 | Cox ...................... B65B 11/045 53/399 |
| 7,386,968 | B2 | 6/2008 | Sperry et al. |
| 7,568,327 | B2 | 8/2009 | Lancaster, III et al. |
| 7,707,901 | B2 | 5/2010 | Lancaster, III et al. |
| 7,779,607 | B2 | 8/2010 | Lancaster, III et al. |
| 8,739,502 | B2 | 6/2014 | Lancaster, III et al. |
| 2004/0031238 | A1 * | 2/2004 | Cox ...................... B65B 11/045 53/399 |
| 2007/0209324 | A1 | 9/2007 | Lancaster, III et al. |
| 2009/0178374 | A1 | 7/2009 | Lancaster, III et al. |
| 2009/0293425 | A1 * | 12/2009 | Carter .................. B65B 11/025 53/167 |
| 2010/0300049 | A1 | 12/2010 | Schmidt et al. |
| 2010/0303526 | A1 | 12/2010 | Hayase |
| 2012/0102887 | A1 | 5/2012 | Lancaster, III et al. |
| 2013/0076753 | A1 | 3/2013 | Lancaster, III et al. |
| 2014/0223864 | A1 | 8/2014 | Lancaster, III et al. |

OTHER PUBLICATIONS

European Patent Office; Search Report and Written Opinion in International Patent Application No. PCT/US2012/056270 dated Jan. 3, 2013; 7 pages.
U.S. Patent and Trademark Office, Office Action issued in related U.S. Appl. No. 13/284,528 dated Jul. 31, 2014.
U.S. Patent and Trademark Office, Final Office Action issued in related U.S. Appl. No. 13/284,528 dated Nov. 5, 2014.
U.S. Patent and Trademark Office, Advisory Action issued in related U.S. Appl. No. 13/284,528 dated Jan. 27, 2015.
U.S. Patent and Trademark Office, Office Action issued in related U.S. Appl. No. 13/284,528 dated Feb. 4, 2015.
U.S. Patent and Trademark Office, Final Office Action issued in related U.S. Appl. No. 13/284,528 dated Oct. 2, 2015.
U.S. Patent and Trademark Office, Office Action issued in related U.S. Appl. No. 13/623,500 dated Nov. 17, 2014.
U.S. Patent and Trademark Office, Final Office Action issued in related U.S. Appl. No. 13/623,500 dated Mar. 27, 2015.

* cited by examiner

| Successful Observed Containment Force Useful Starting Point | | | |
|---|---|---|---|
| Load Cat 1 | Load Cat 2 | Load Cat 3 | Load Cat 4 |
| Very Light Loads | Stable Mid-weight Loads | Heavy Unstable Loads | Very Unstable Loads |
| Paper Towels Empty PET Bottles Empty Containers | Square or short Cartons, Beverage in Trays | Tall Narrow cartons, Unstable Beverage containers | PET Water- shrink wrap bundles |
| 2-5 lbs | 5-7 lbs | 7-12 lbs | 12-20 lbs |

FIG. 8

MACHINE GENERATED WRAP DATA

CROSS-REFERENCE TO RELATED APPLICATIONS

This application is a continuation-in-part of U.S. patent application Ser. No. 13/284,528 filed Oct. 28, 2011, which claims the priority benefit of U.S. Provisional Patent Application No. 61/408,543 filed Oct. 29, 2010. This application is also a continuation of U.S. patent application Ser. No. 13/623,500 filed Sep. 20, 2012, which claims the priority benefit of U.S. Provisional Patent Application No. 61/538,373 filed Sep. 23, 2011. The disclosures of all of these applications are incorporated by reference herein in their entirety.

TECHNICAL FIELD

The present disclosure relates to methods and apparatus for wrapping loads with a wrapping machine, and more particularly, for generating wrap data with the wrapping machine.

BACKGROUND

An important consideration when wrapping loads with packaging material, and then shipping the wrapped loads, is whether the packaging material is applied to the load with enough layers to generate a level of containment force on the load that is adequate for keeping the load intact during shipping. This must be weighed against other considerations including, for example, the weight and cost of packaging material used to wrap each load. Determining the effectiveness of packaging materials for wrapping loads requires an understanding of these and other considerations.

For many reasons, the effectiveness of packaging materials for wrapping loads is difficult to quantify and predict. In production facilities where loads are wrapped with packaging material, typically no methods are employed to measure the requirements or characteristics of an effectively wrapped load, since operators of such facilities focus on meeting shipment rates rather than on determining the quality of wrapping on the loads in those shipments.

In some instances, data has been generated manually after wrapping of a load using measuring devices including, for example, containment force measuring tools and scales. However, due to the time and effort required to generate and analyze such data, generating and analyzing the data is often ignored, increasing the likelihood that a wrapped load that is transported may have a containment force below that which is needed for successfully transporting the wrapped load, and thus, risking failure of the wrapped load during transport. Such failures may be costly since the load may be damaged or may damage transportation equipment, and/or may cause delays or missed deliveries. Failing to generate and analyze data may also lead to loads being wrapped with more film than is actually needed, leading to inefficiency and higher costs.

In other instances, data has been generated by cutting packaging material off of a wrapped load and performing analyses on the cut packaging material. Generating data this way is wasteful and time consuming. And since cutting the packaging material off of every wrapped load is not desirable, cutting is typically performed on a single test load, and an assumption is made that the results are consistent for subsequent loads. This may not be the case, however, if the characteristics of the loads being wrapped vary, if the packaging material is changed, or if wrap settings are adjusted.

Another difficulty arises due to there being several packaging material manufacturers in the marketplace, many offering several different types of packaging materials, as well as variants of those types. All of these different packaging materials may have different characteristics that impact their effectiveness for wrapping loads. In addition, a first operator of a wrapping machine may use settings that are different from those used by a second operator of the wrapping machine, thus adding further variability to the process. The number of potential combinations of variables adds to the complexity of determining the effectiveness of packaging materials.

Another important consideration when wrapping loads with packaging material is the number of film breaks that occur per roll of film or per wrapped load. The ability to maintain the number of film breaks per roll of film or wrapped load at or below a maximum tolerated value assists in maintaining a minimum required containment force, reduces the amount of film required to wrap a given load, increases wrapping machine uptime and machine operator productivity, and guides the set up choices for a machine operator when setting up the wrapping machine to wrap loads.

The present disclosure is directed to overcoming one or more of the above-noted problems.

SUMMARY

According to one aspect of the present disclosure, a method may be provided for generating data during wrapping of a load with a wrapping machine, where the wrapping machine includes a packaging material dispenser. The method may include determining with a sensing assembly a number of relative revolutions between the packaging material dispenser and the load during wrapping of the load and a height of the packaging material dispenser relative to the load during each relative revolution, and determining a number of layers applied to a face of the load at one or more heights based on the determined number of relative revolutions and height, where the number of layers applied to the face of the load at the one or more heights is representative of a thickness of packaging material applied to the face of the load at the one or more heights.

According to another aspect of the present disclosure, a method may be provided for generating data during wrapping of a load with a wrapping machine, where the wrapping machine includes a packaging material dispenser. The method may include determining a number of relative revolutions between the packaging material dispenser and the load during wrapping of the load with a sensing assembly on the wrapping machine, determining a height of the packaging material dispenser relative to the load during each relative revolution, determining a number of layers applied to a face of the load at one or more heights based on the determined number of relative revolutions and the determined height of the packaging material dispenser relative to the load during each relative revolution, where the number of layers applied to the face of the load at the one or more heights is representative of a thickness of packaging material applied to the face of the load at the one or more heights, and displaying a graph on a display device, the graph including an axis indicative of the face of the load and one or more indicators along the axis indicative of the thickness of packaging material applied to the face of the load at the one or more heights.

According to yet another aspect of the present disclosure, a method may be provided for generating data during wrapping of a load with a wrapping machine, the wrapping machine including a packaging material dispenser. The method may include determining a number of relative revolutions between the packaging material dispenser and the load during wrapping of the load with a sensing assembly on the wrapping machine, determining a height of the packaging material dispenser relative to the load during each relative revolution, determining a value indicative of a containment force exerted on the load by packaging material applied to the load during wrapping at one or more heights based on the determined number of relative revolutions, the determined height of the packaging material dispenser relative to the load during each relative revolution, and a value indicative of an individual containment force exerted on the load by each layer of packaging material applied to the load, and displaying a graph on a display device, the graph including an axis indicative of a face of the load and one or more indicators along the axis indicative of the containment force applied to the face of the load at the one or more heights.

According to another aspect of the present disclosure, a method may be provided for generating data during wrapping of a load with a wrapping machine. The method may include storing a value for a characteristic associated with a packaging material by wrapping a test load with the packaging material and measuring the characteristic, where the characteristic is indicative of a containment force exerted on the test load by one layer of the packaging material, sensing with a sensing assembly on the wrapping machine relative rotation between a packaging material dispenser and a second load different from the test load during wrapping of the second load, determining at least one parameter associated with the packaging material dispensed to the wrapped second load based on the sensed relative rotation and the obtained value without removing the packaging material from the wrapped second load, where the at least one determined parameter includes a containment force exerted by the packaging material on the wrapped second load, and displaying information associated with the at least one parameter on a display device.

According to yet another aspect of the present disclosure, a method may be provided for generating data during wrapping of a load with a wrapping machine, the wrapping machine including a packaging material dispenser. The method may include determining with a sensing assembly a number of relative revolutions between the packaging material dispenser and the load during wrapping of the load and a height of the packaging material dispenser relative to the load during each relative revolution, determining a value indicative of a containment force exerted on the load by packaging material applied to the load during wrapping at one or more heights based on the determined number of relative revolutions, the determined height of the packaging material dispenser relative to the load during each relative revolution, and a value indicative of an individual containment force exerted on the load by each layer of packaging material applied to the load, determining based upon the value whether the load meets a predetermined minimum required containment force standard for the load, and displaying information on a display device indicating whether the load meets the predetermined minimum required containment force standard for the load.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

The accompanying drawings, which are incorporated in and constitute a part of this specification, illustrate embodiments of the present disclosure and together with the description, serve to explain the principles of the present disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The disclosures of each of U.S. Patent Application Publication No. 2011/0131927, entitled "DEMAND BASED WRAPPING," filed Nov. 6, 2010; U.S. Patent Application Publication No. 2009/0178374, entitled "ELECTRONIC CONTROL OF METERED FILM DISPENSING IN A WRAPPING APPARATUS," filed Jan. 7, 2009; U.S. Pat. No. 7,707,901, entitled "APPARATUS AND METHOD FOR MEASURING CONTAINMENT FORCE IN A WRAPPED LOAD AND A CONTROL PROCESS FOR ESTABLISHING AND MAINTAINING A PREDETERMINED CONTAINMENT FORCE PROFILE," filed Apr. 21, 2008; U.S. Pat. No. 7,779,607, entitled "WRAPPING APPARATUS INCLUDING METERED PRE-STRETCH FILM DELIVERY ASSEMBLY," filed Feb. 23, 2007; U.S. Pat. No. 7,568,327, entitled "METHOD AND APPARATUS FOR SECURING A LOAD TO A PALLET WITH A ROPED FILM WEB," filed Jan. 30, 2004; U.S. Patent Application Publication No. 2007/0209324, entitled "METHOD AND APPARATUS FOR SECURING A LOAD TO A PALLET WITH A ROPED FILM WEB," filed Feb. 23, 2007, are incorporated herein by reference in their entirety. Examples and descriptions of the disclosure are also set forth in the disclosure materials that are included as part of this application and are incorporated herein by reference.

Figure 1:
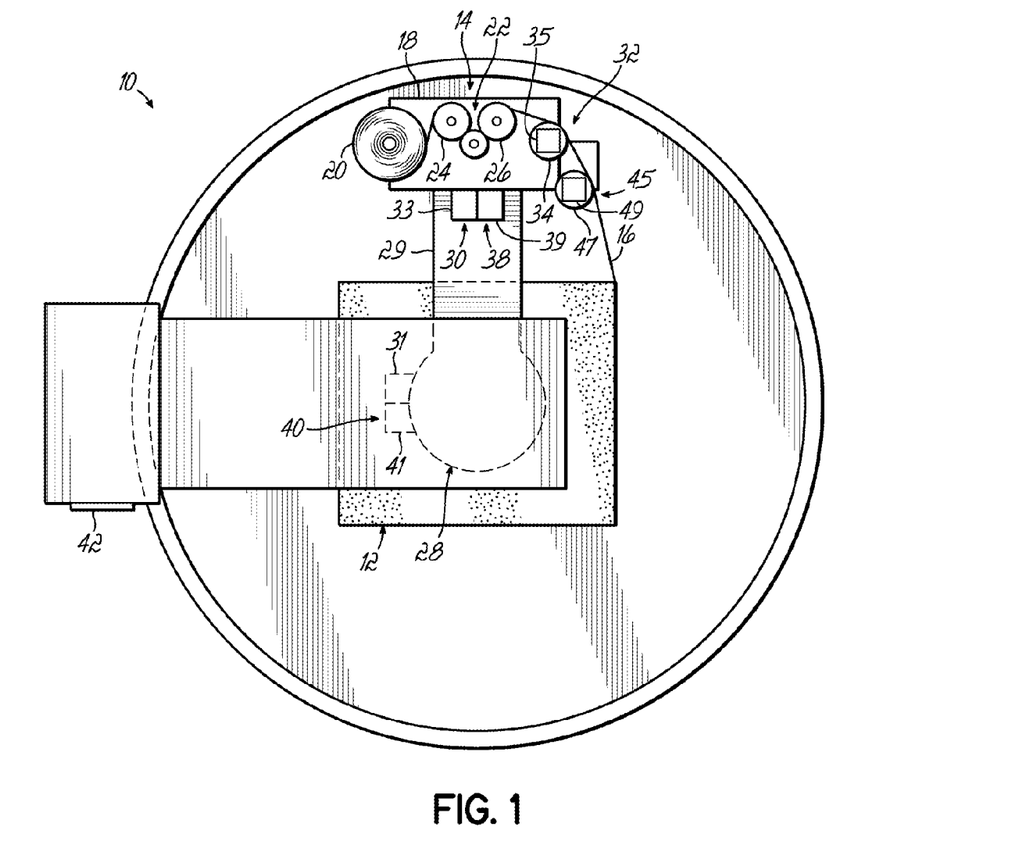
FIG. 1 is a top view of a wrapping machine, according to an aspect of the present disclosure.

According to one aspect of this disclosure, a wrapping machine 10 for wrapping a load 12, is shown in FIG. 1. The wrapping machine 10 may include a packaging material dispenser 14 for dispensing packaging material 16. The packaging material dispenser 14 may include a roll carriage 18 configured to support a roll 20 of the packaging material 16. The packaging material 16 may include stretch wrap packaging material. Stretch wrap packaging material has a high yield coefficient to allow the material to undergo stretching during wrapping. Alternatively, the packaging material 16 may include netting, strapping, banding, or tape.

The packaging material dispenser 14 may also include one or more packaging material dispensing rollers 22 configured to receive packaging material 16 from the roll 20 and dispense the packaging material 16 for application to the load 12. The one or more packaging material dispensing rollers 22 may be driven for rotation about their respective axes by a drive system (not shown) including, for example, an electric motor or any other suitable power source, similar to that which is described in U.S. Patent Application Publication No. 2009/0178374.

The one or more packaging material dispensing rollers 22 may include prestretch rollers 24 and 26. The prestretch rollers 24 and 26 are configured to stretch the packaging material 16 before the packaging material 16 is dispensed to the load 12. The prestretch rollers 24 and 26 stretch the packaging material 16 by engaging a portion of the packaging material 16 with the upstream prestretch roller 24, which rotates at a slower speed than the downstream prestretch roller 26, while also engaging a portion of the packaging material 16 with the downstream prestretch roller 26. The disparity between the rotational speeds of the prestretch rollers 24 and 26 cause stretching of the portion of the packaging material 16 between the prestretch rollers 24 and 26.

The wrapping machine 10 may also include a relative rotation assembly 28 for providing relative rotation between the packaging material dispenser 14 and the load 12. The relative rotation assembly 28 may include a drive system 31 including, for example, an electric motor or any other suitable power source, similar to that which is described in U.S. Patent Application Publication No. 2009/0178374. The relative rotation assembly 28 may also include a rotating arm 29, a rotatable turntable (not shown), or a rotating ring (not shown), powered by the drive system, as described in U.S. Patent Application Publication No. 2009/0178374.

The wrapping machine 10 may also include a vertical drive assembly 30 for providing relative vertical movement between the packaging material dispenser 14 and the load 12. The vertical drive assembly 30 may include a drive system 33 including, for example, an electric motor or any other suitable power source, similar to that which is described in U.S. Patent Application Publication No. 2009/0178374. The combined operation of the vertical drive assembly 30 and the relative rotation assembly 28 carries the packaging material dispenser 14 along a substantially spiral path relative to the load 12 to spirally wrap the packaging material 16 around the load 12.

Figure 5:
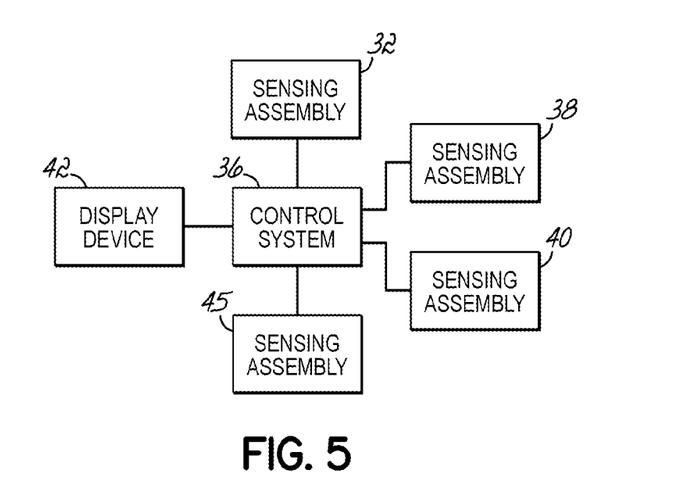
FIG. 5 is a schematic diagram depicting a control system and sensing assemblies, according to an aspect of the present disclosure.

The wrapping machine 10 also includes a sensing assembly 32 configured to sense a characteristic of the packaging material 16. The sensing assembly 32 may be similar to that which is described in U.S. Patent Application Publication No. 2009/0178374. For example, the sensing assembly 32 may include a roller 34, which may be an idle or unpowered roller, that is rotatably mounted on the packaging material dispenser 14. The roller 34 may engage the packaging material 16 that is dispensed from the packaging material dispenser 14. Thus, rotation of the roller 34 may provide an indication of an amount of the packaging material 16 dispensed from the packaging material dispenser 14 to the load 12. The sensing assembly 32 may also include a sensing device 35 for sensing rotation of the roller 34. The sensing device 35 may include any suitable reader, encoder, transducer, detector, or sensor capable of sensing rotation of the roller 34. Signals from the sensing assembly 32, indicative of the sensed rotation of the roller 34, may be sent to a control system 36 of the wrapping machine 10, as shown in FIG. 5. The sensing assembly features described above are exemplary, and it is contemplated that in addition to, or as an alternative to, the above described features, a photoeye, proximity detector, laser distance measurer, ultrasonic distance measurer, electronic rangefinder, and/or any other suitable distance measuring device, may be used.

The wrapping machine 10 may also include a sensing assembly 38 configured to sense a height of at least a portion of the packaging material dispenser 14 relative to the load 12. The portion of the packaging material dispenser 14 may include, for example, the roll carriage 18. The sensing assembly 38 may include a sensing device 39 configured to sense the height of the roll carriage 18 relative to the load 12, and provide a signal indicative of the relative height to the control system 36. The sensing device 39 may include any suitable reader, encoder, transducer, detector, or sensor capable of determining the height of the roll carriage 18 relative to the load 12.

The wrapping machine 10 may also include a sensing assembly 40 configured to sense the relative rotation of the packaging material dispenser 14 relative to the load 12 that is provided by the relative rotation assembly 28. The sensing assembly 40 may include a sensing device 41 configured to sense rotation of the electric motor or other power source driving the relative rotation, and provide a signal indicative of the relative rotation to the control system 36. The sensing assembly 40 may include any suitable encoder, transducer, reader, detector, or sensor.

The control system 36 may include a processor, a computer, or any other suitable computing and controlling device configured to run software and control machine operations. The control system 36 may receive signals from the sensing assemblies 32, 38, and 40 and make determinations based thereon, and may also be configured to control operation of the packaging material dispenser 14, relative rotation assembly 28, and vertical drive assembly 30, by sending instruction signals to the drive systems in those assemblies, similar in manner to what is described in U.S. Patent Application Publication No. 2009/0178374.

Figure 2:
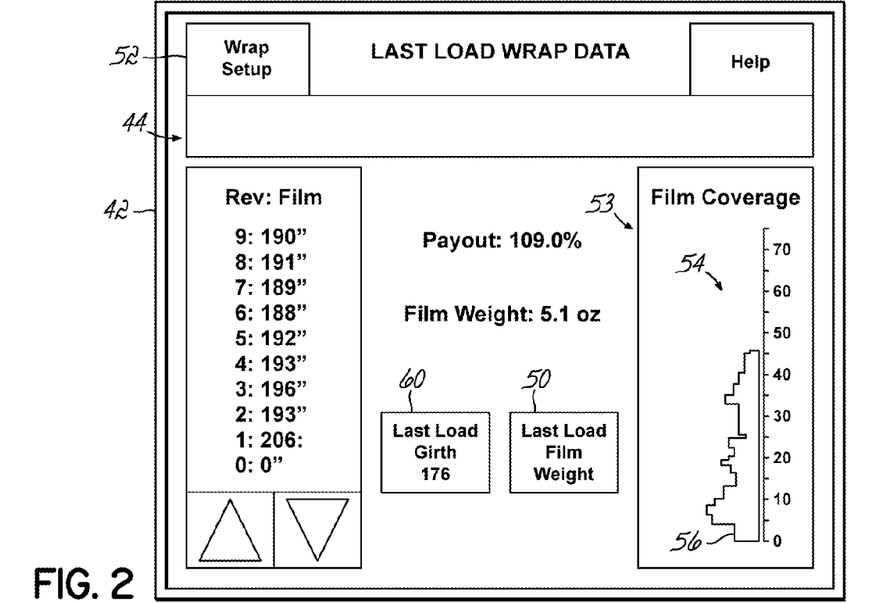
FIG. 2 is an exemplary screen shot on a display device, according to an aspect of the present disclosure.
Figure 3:
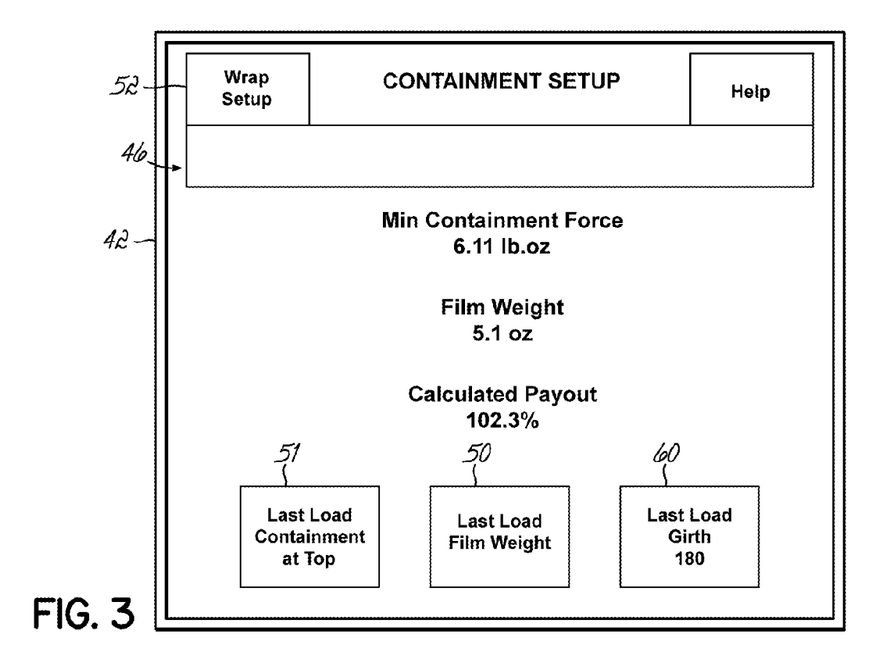
FIG. 3 is another exemplary screen shot on a display device, according to an aspect of the present disclosure.
Figure 4:
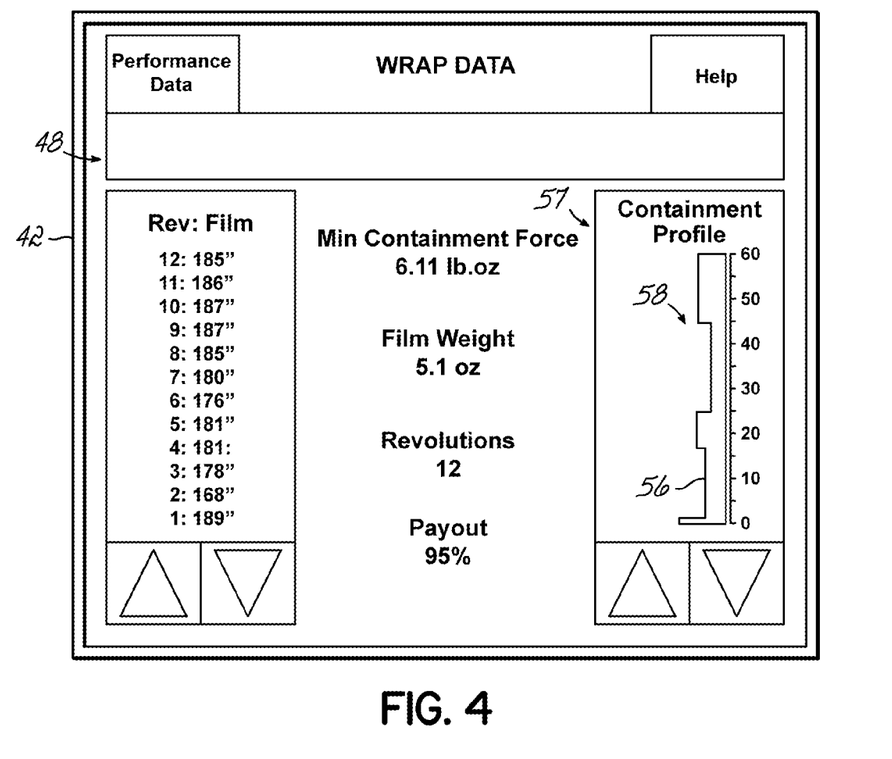
FIG. 4 is another exemplary screen shot on a display device, according to an aspect of the present disclosure.

The control system 36 (FIG. 5) may generate output signals and values, at least some of which may be displayed on a display device 42 of the wrapping machine 10. Screen shots 44, 46, and 48 from the display device 42, showing the output signals and values, are depicted in FIGS. 2-4. The display device 42 may include, for example, a touch screen display mounted on a surface of the wrapping machine 10, and/or a display on a remote electronic device, such as a computer, smartphone, or similar device. The display device 42 may also be configured to receive inputs from a user by displaying a keypad, a keyboard, list, table, menu, and/or any other suitable input tool.

According to one aspect of this disclosure, methods for generating data for display on the display device 42 are provided. One of these methods is used to determine the weight of the packaging material 16 used to wrap a load so it can be displayed on the display device 42. The method includes establishing baseline weight per inch values for one or more types of packaging material. Establishing a baseline weight per inch value for the packaging material 16 may begin with performing a wrap cycle to wrap a baseline or test load with the packaging material 16. During the wrap cycle, the control system 36, using the sensing assembly 32, may keep track of the length of the packaging material 16 dispensed during wrapping. For example, the length of the packaging material 16 dispensed during wrapping can be calculated by multiplying the number of revolutions undergone by the roller 34 during wrapping by the circumference of the roller 34.

After the baseline load has been wrapped, the packaging material 16 wrapped around the baseline load is cut from the baseline load and is weighed on a scale. The weight of the packaging material 16 cut from the baseline load is entered into the control system 36 using the display device 42.

The control system 36 may divide the weight of the packaging material 16 cut from the baseline load by the length of the packaging material 16 dispensed during wrapping to determine the weight per inch of the packaging material 16. The weight per inch value of the packaging material 16 may be stored in a memory location by the control system 36. It is contemplated that the above-recited steps for determining the weight per inch value of the packaging material 16 may be carried out on different types of packaging material to develop a library of weight per inch values for many different types of packaging material. The library may be accessed by the control system and/or a user.

When a user wants to wrap loads for shipping, the user will input the weight per inch value for the type of packaging material the user is using into the control system 36. The user may do so by pressing, for example, a button 52 shown in FIGS. 2 and 3. Once the button 52 has been pressed, the display device 42 may provide the user with a suitable input tool by which the user can enter the weight per inch value, and/or type in one or more identifiers associated with the packaging material so the control system 36 can obtain the weight per inch value from the library. It is also contemplated that the user may be provided with a list or menu of packaging materials on the display device 42. The user may choose the packaging material from the list or menu, and the control system 36 may obtain the corresponding weight per inch value from the library.

Once the weight per inch value has been entered, the user's load is wrapped. During wrapping of the user's load, the control system 36 may use signals from the sensing assembly 32 to determine the length of the packaging material 16 dispensed during wrapping. The length dispensed is multiplied by the weight per inch value for the packaging material 16 to determine the weight of the packaging material 16 used to wrap the user's load. It should be understood that the weight per inch value remains accurate even if the users load has different dimensions or characteristics than the baseline load, and/or is wrapped using a different wrapping pattern or different settings than those used to wrap the baseline load. However, if the type of packaging material the user is using to wrap the loads changes, by inputting or selecting the weight per inch value associated with the new packaging material before wrapping subsequent loads, the user may ensure that the calculated weight dispensed is accurate.

The weight of the packaging material 16 used to wrap the user's load may be displayed on the display device 42, as shown in FIGS. 2-4. The weight of the packaging material 16 used to wrap the previous load may be accessed by touching a button 50. By this process, the user is automatically provided with a visual indication of the weight of the packaging material 16 being used to wrap the users loads for each of the wrapped loads. The user may make adjustments to the wrapping process and/or to the packaging material used, if the weight of the packaging material 16 being used is outside of a desired range of values. It is also contemplated that the control system 36 may be provided with the desired range of weight values, and if the weight of the packaging material 16 is outside of that range, a warning may be displayed on the display device 42 to alert the user. The warning may be in the form of an audible alarm, colored text or symbols, flashing text or symbols, and/or animations on the display device 42. Additionally or alternatively, an e-mail or other electronic communication may be sent to one or more remote electronic devices to alert the user.

It is contemplated that if the cost per weight of the packaging material 16 can be determined, the weight per inch value may be converted into a cost per inch value. Using the process described above, the cost of the packaging material 16 used to wrap the users load may be determined and displayed on the display device 42, with warnings being communicated to the user when the cost is outside of a desired range of values.

According to an aspect of the present disclosure, another method for generating and displaying data may include determining wrap profile data 53 and/or 57, and displaying the wrap profile data 53 and/or 57, as shown in FIGS. 2 and 4, on the display device 42. As shown in FIG. 2, the wrap profile data 53 provides the user with a visual indication of the thickness of packaging material 16 (e.g., the number of layers of the packaging material 16) wrapped onto a face of the load 12.

In order for such data to be generated and displayed, the user may first input an effective height of the packaging material 16 into the control system 36 via the display device 42. The user may input the effective height via the display device 42 in a manner similar to entry of the weight per inch value. The effective height of the packaging material 16 is a height of the packaging material 16 dispensed from the packaging material dispenser 14 as measured from a first edge of the dispensed packaging material 16 to a second edge of the dispensed packaging material 16, the second edge being opposite the first edge. The first edge and the second edge may be defined by portions of the packaging material 16 that are not roped or rolled into a cable. It is also contemplated that at least one of the first edge and the second edge may be an edge portion of a rope or rolled cable formed from the packaging material 16.

The control system 36 generates a graph 54, shown in FIG. 2, with the y-axis (vertical) of the graph 54 representing a face of the load 12 to be wrapped. The x-axis (horizontal) of the graph 54 is indicative of the thickness of packaging material 16 on the face of the load 12. As the load 12 is wrapped, the control system 36, using signals from the sensing assemblies 40 and 38, monitors the number of relative revolutions of the packaging material dispenser 14 and the height of the packaging material dispenser 14 relative to the load at which the revolutions take place. By using this information, as well as the user-inputted effective height of the packaging material 16, one or more bars 56 or other suitable indicators may be generated along the x-axis of the graph 54.

For example, during wrapping, packaging material having a twenty inch effective height may be used to wrap the load 12. Based on the signal from the sensing assembly 38, the control system 36 may determine the height on the face of the load 12 at which the packaging material is dispensed and applied to the face of the load 12. Based on the signal from the sensing assembly 40, the control system 36 can determine the number of relative rotations of the packaging material dispenser 14 relative to the load 12 at each height during wrapping. Thus, if the control system 36 determines, based on the signal from the sensing assembly 38, that the bottom twenty inches of the load 12 is being wrapped, and that, based on the signal from the sensing assembly 40, there have been three relative rotations between the packaging material dispenser 14 and the load 12 at that height, the control system 36 will update the graph 54 to display three bars on the x-axis for each unit of height on the y-axis between 0 and 20 (representing the portion of the face of the load 12 between a bottom edge of the load 12 and a point twenty inches above the bottom edge).

If the control system 36 determines that the fourth relative revolution is performed with the packaging material dispenser 14 at a height relative to the load 12 indicating that the relative revolution took place with the packaging material dispenser 14 wrapping the portion of the load 12 between ten and thirty inches from the bottom of the load 12, the control system 36 will update the graph 54 by adding one bar on the axis for each unit of height on the y-axis between 10 and 30, such that there would be three bars on the x-axis at the unit of height between 0 and 10 on the y-axis, four bars on the x-axis for each unit of height between 10 and 20 on the y-axis, and one bar on the x-axis for each unit of height between 20 and 30. This process is carried out throughout wrapping of the load 12 to generate a profile of the thickness of packaging material 16 on the face of the load 12. In FIG. 2, the bars 56 on the graph 54 display an exemplary profile associated with a wrapped load, and not necessarily the wrapped load from the example above.

It is contemplated that the user can input data into the control system 36 indicating that an edge portion of the packaging material 16 includes a rope or rolled cable of film, similar to that which is described in U.S. Pat. No. 7,568,327 and U.S. Patent Application Publication No. 2007/0209324. Additionally or alternatively, a sensing assembly (not shown) may be provided on the wrapping machine 10 that can determine whether a drive down and roping assembly, similar to that which is described in U.S. Pat. No. 7,568,327 and U.S. Patent Application Publication No. 2007/0209324, has been actuated during wrapping to rope or roll the packaging material 16. The control system 36 may use this information when updating the graph 54. For example, if the control system 36 is informed that an edge portion of the twenty inch high packaging material 16 includes a rope or rolled cable, giving the edge portion added thickness, the control system may add multiple bars on the x-axis of the graph 54 at the height on the y-axis corresponding to the height on the face of the load 12 at which the rope or rolled cable is applied, while adding a single bar on the x-axis for heights on the y-axis corresponding to portions on the face of the load 12 at which a non-roped or non-rolled portion of the packaging material 16 is applied. For example, when the bottom twenty inches of the load is being wrapped with twenty-inch high packaging material 16 that includes a rope or rolled cable at its bottom edge, for each relative revolution between the packaging material dispenser 14 and the load 12, the control system may add multiple bars on the x-axis for each unit of height between 0 and 1 on the y-axis while adding one bar on the x-axis for each unit of height between 1 and 20 on the y-axis of the graph 54.

Since each layer of packaging material 16 exerts a force on the surface of the load 12, it should be understood that the profile displayed on the graph 54 is indicative of the thickness or number of layers of packaging material 16 on the face of the load 12, as shown in FIG. 2, and is also indicative of the force exerted on the face of the load 12 by the packaging material 16 wrapped thereon. Thus, a graph 58 shown in FIG. 4 may be generated in a manner similar to the graph 54 of FIG. 2. In FIG. 4, the bars 56 on the graph 57 display an exemplary profile associated with a wrapped load, and not necessarily the same wrapped load that produced the profile shown in FIG. 2. It should be understood, however, that if graphs 54 and 57 are generated based on the same wrapped load, the bar profiles on the graphs may be substantially identical.

By displaying the graphs 54 and/or 58 on the display device 42, the user is able to see the distribution of packaging material 16 and/or force on the face of the load easily. The user may be able to identify areas of excess packaging material 16 and/or force, areas of undesirably low packaging material coverage and/or force, and areas that have not been covered at all by packaging material 16 and have no containment force acting thereon. For example, areas of lower packaging material coverage and/or the area with the lowest packaging material coverage, may be highlighted on the graphs 54 and/or 58 using different colored bars, text, symbols, and/or animation to catch the attention of an observer.

The user may use this information to make adjustments to wrapping parameters to achieve a more desirable profile. For example, the user (and/or any other machine operator) may adjust the wrapping pattern for wrapping a subsequent load based on the graphs 54 and/or 58 for a previously wrapped load by having the packaging material dispenser 14 dispense more of the packaging material 16 at areas of the load to be wrapped corresponding to areas on the graphs 54 and/or 58 with a lower number of bars than other areas, and less of the packaging material 16 at areas of the load to be wrapped corresponding to areas on the graphs 54 and/or 58 with a higher number of bars than other areas.

According to an aspect of this disclosure, another method for generating and displaying data may include determining the area on the face of a wrapped load at which the packaging material 16 is exerting the least force on the load. Identifying the location and characteristics of this area is desirable since it provides an indication of the area of the wrapped load at which failure of the packaging material 16 is most likely to occur. As long as the force at that area is in a desired range, the user can be assured that the probability of packaging material failure during shipping of a wrapped load has been minimized or at least reduced to an acceptable level of risk.

One or more baseline values can be found by inputting a girth of a baseline or test load and setting the wrapping machine 10 to wrap the baseline load at a payout percentage of 100%. The girth may be found by manually measuring dimensions of the load, by automatically sensing boundaries of the load with sensing devices, and/or by any other suitable method. The girth may be entered using the display device 42 by accessing an input tool via a button 60 shown in FIGS. 2 and 3. The payout percentage is a measure of the length of packaging material 16 dispensed during one relative revolution divided by a girth of the load to be wrapped. A payout percentage of 100% means that the length of packaging material 16 dispensed during one relative revolution of the packaging material dispenser 14 relative to the baseline load is equal to the girth of the baseline load. The payout percentage value for wrapping the baseline load can be input into the control system 36 by touching the button 52 to access any suitable input tool.

Using a containment force measuring device (not shown) like the one described in U.S. Pat. No. 7,707,901, a measurement of the containment force at a point on the wrapped baseline load may be taken. The point may be at the top of the wrapped baseline load, for example. The containment force value may be entered into the control system 36 using any suitable input tool accessed by touching a button 51 shown in FIG. 3. The control system 36 may determine the number of relative revolutions the packaging material dispenser 14 made relative to the baseline load during wrapping at the measurement point, which is indicative of the number of layers of packaging material 16 on the face of the wrapped baseline load at the measurement point. The control system 36 may divide the measured containment force value by the number of relative revolutions to determine the containment force exerted by each layer of the packaging material 16 at the measurement point, thus arriving at the force per relative revolution or layer of the packaging material 16. The calculated force per relative revolution value is a baseline value usable in other calculations. It should be understood that a library of baseline values with values categorized based on wrapping conditions may be stored by the control system 36, and thus, the baseline values would be available for selection by the user from a list or menu (not shown) without requiring wrapping a baseline load.

When the user wants to wrap a load 12 for shipping, the control system 36 will have already been provided with the baseline force per relative revolution value, as well as the girth of the load 12 being wrapped. Based on signals from the sensing assemblies 32 and 40, the control system may determine the amount of packaging material 16 dispensed during a relative revolution between the packaging material dispenser 14 and the load. The control system 36 may calculate the payout percentage value at which the load is being wrapped by dividing the amount dispensed during the relative revolution by the girth of the load. The calculated payout percentage may be displayed on the display device 42, as shown in FIGS. 2-4.

The control system 36 may determine the containment force per revolution or layer of packaging material applied to the load during wrapping by starting with the baseline force per relative rotation value and adjusting it by a factor based on the difference between the payout percentage of 100% used to determine the baseline force per relative rotation value and the calculated payout percentage. Adjustment is necessary because if the calculated payout percentage is 110%, a greater amount of material is being dispensed per relative rotation than when wrapping at 100%, and thus, each layer wrapped at 110% exerts less force on the load than the layers wrapped at 100%. It is contemplated that for calculated payout percentages over 100%, the baseline force per relative revolution may be multiplied by a factor calculated by taking a difference between the baseline force per relative revolution and the calculated payout percentage, subtracting that from 100%, and dividing by 100. In this example, the factor would be 0.9.

On the other hand, if the calculated payout percentage is 90%, a smaller amount of material is being dispensed per relative rotation than when wrapping at 100%, and thus, each layer wrapped at 90% exerts more force on the load than the layers wrapped at 100%. It is contemplated that for calculated payout percentages under 100%, the baseline force per relative revolution may be multiplied by a factor calculated by taking a difference between the baseline force per relative revolution and the calculated payout percentage, adding that to 100%, and dividing by 100. In this example, the factor would be 1.1.

During wrapping of the load, the control system 36 may update the graph 54 and/or the graph 58 such that the user is able to view the wrap profile for the wrapped load when wrapping has been completed. The control system 36 may also flag the height on the graph 54 and/or the graph 58 having the least number of bars, that height being indicative of the weak area on the wrapped load, and store the number of bars at the weak area in memory. The control system 36 may calculate the minimum containment force on the wrapped load by multiplying the containment force per revolution or layer of packaging material by the number of bars or layers in the weak area. It is also contemplated that the weak area may be highlighted on the display device 42 by, for example, the use of color, text, animation, and/or any other suitable identifiers to inform a viewer of the location of the weak area on the graph 54 and/or the graph 58. The control system 36 may display the minimum containment force on the display device 42, as shown in FIGS. 3 and 4.

By this process, the user is automatically provided with a visual indication of the minimum containment force on each of the users wrapped loads. The user may make adjustments to the wrapping process and/or to the packaging material used, if the minimum containment force is outside of a desired range of values, such as a known range of values that typically survive being transported. It is also contemplated that the control system 36 may be provided with the desired range of values, and thus, if the minimum containment force is outside of that range, a warning may be displayed on the display device 42 to alert the user. The warning may be in the form of an audible alarm, colored text or symbols, flashing text or symbols, and/or animation on the display device. Additionally or alternatively, an e-mail of other electronic communication may be sent to remote electronic devices to alert the user.

The user may use this information to make adjustments to wrapping parameters to achieve a more desirable profile. For example, the user (and/or any other machine operator) may adjust the wrapping pattern for wrapping a subsequent load based on the graphs 54 and/or 58 for a previously wrapped load by having the packaging material dispenser 14 dispense more of the packaging material 16 at the area associated with the minimum containment force, and less of the packaging material 16 at other areas. It is contemplated that the control system may take an average of the number of bars for a range of heights that includes the height having the least number of bars or minimum containment force. For example, the control system 36 may take an average of the number of bars for a range extending four inches above and below the height having the least number of bars, identify that entire range as the weak area, and multiply that average number of bars for the range by the containment force per revolution to calculate the minimum containment force. The entire range may be identified by highlighting, text, symbols, and/or animation, making it easier for a machine operator to see where weak areas exist, and set the wrapping pattern to compensate due to the weak area forming a larger target.

As shown in the screen shots 44 and 48 of FIGS. 2 and 4, the length of the packaging material 16 dispensed during each relative revolution between the packaging material dispenser 14 and the load 12 may be displayed for viewing by the user. Data for the length dispensed during each relative revolution may come from the sensing assembly 32, which provides the control system 36 with data on the length of the packaging material 16 dispensed, and the sensing assembly 40, which provides the control system 36 with data on the relative revolutions of the packaging material dispenser 14 relative to the load 12. Using the sensing assemblies 32 and 40, the control system 36 is aware of when a relative revolution starts and ends, and how much packaging material 16 was dispensed during that time period. That information is then displayed on the display device 42.

Displaying such information serves a diagnostic function, allowing a machine operator or observer to determine whether the amount of the packaging material 16 dispensed per relative revolution, and per load girth, is within a desired range. For example, an observer may compare the amount of the packaging material 16 dispensed per relative revolution to the load girth to see if the commanded payout percentage is being met. Additionally or alternatively, the display device 42 may also show whether a variation in load girth has been encountered during wrapping. The display device 42 may also show variations in payout during different relative revolutions. For example, the display device 42 may show that the payout of the packaging material 16 is different during the first and/or last relative revolutions, as compared to the relative revolutions therebetween, to set up the packaging material 16 for proper clamping, cutting, and wiping. It is also contemplated that summing the lengths shown in the display device 42 may provide the input for calculations requiring data on the length of the packaging material 16 dispensed, such as the film weight calculation described in preceding paragraphs.

Referring back to FIG. 1, the wrapping machine 10 may also include a sensing assembly configured to sense breaks in the packaging material 16 during wrapping of a load. This packaging material break sensing assembly may be similar to that which is described in U.S. Patent Application Publication No. 2009/0178374 and/or U.S. Patent Application Publication No. 2011/0131927. The function of this packaging material break sensing assembly may be incorporated into the sensing assembly 32 previously described, or a separate sensing assembly 45 may be provided for sensing breaks in the packaging material 16. For example, the sensing assembly 45 may include a roller 47, which may be an idle or unpowered roller that is rotatably mounted on the packaging material dispenser 14 and which engages the packaging material 16 that is dispensed from the packaging material dispenser 14, and a sensing device 49 for sensing rotation of the roller 47. The sensing device 49 may include any suitable reader, encoder, transducer, detector, or sensor capable of sensing rotation of the roller 47. Signals from the sensing assembly 45, indicative of breaks occurring in the packaging material 16 during wrapping, may be sent to the control system 36 of the wrapping machine 10, as shown in FIG. 5. For example, if the number of pulses detected by sensing device 45 is less than the expected number of pulses, the control system 36 may recognize that a break has occurred.

Figure 6:
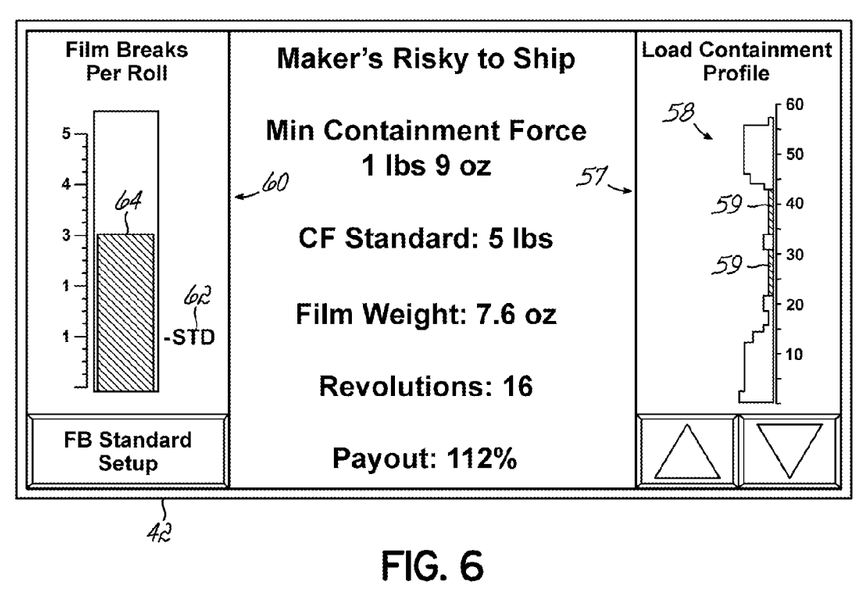
FIG. 6 is another exemplary screen shot on a display device, according to an aspect of the present disclosure.
Figure 7:
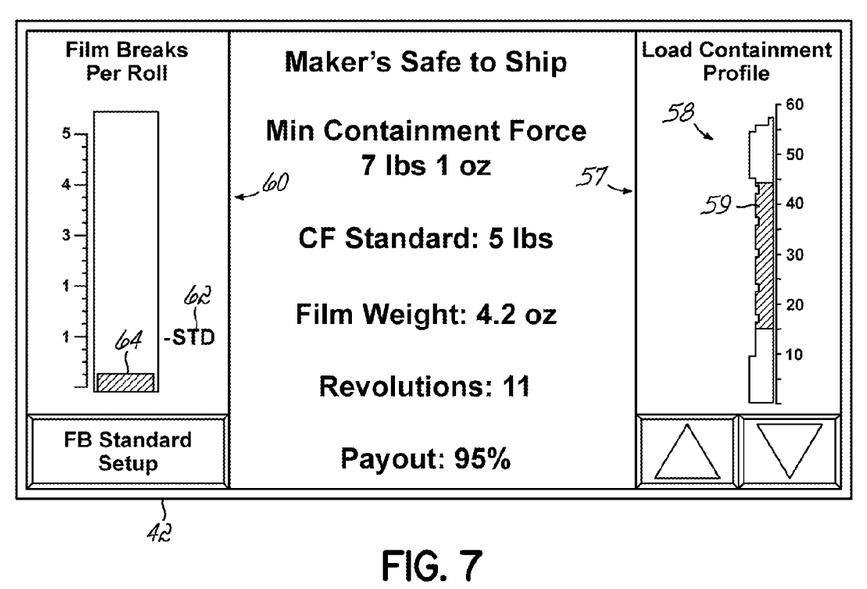
FIG. 7 is another exemplary screen shot on a display device, according to an aspect of the present disclosure.

According to another aspect of the disclosure, another method for generating and displaying data may include determining wrap profile data 57 and/or 60, and displaying the wrap profile data 57 and/or 60 on the display device 42, as seen in FIGS. 6 and 7. Referring first to FIG. 6, as described above, the profile data 57 displayed in graph 58 is the load containment force profile. The profile data 57 displayed in graph 58 also corresponds to the thickness or number of layers of packaging material 16 on the face of the load 12, as discussed above in connection with the discussion of FIGS. 2 and 4. The indicators, bars, or areas 59 in the graph 58 are those areas in the load profile that exhibit the minimum or lowest containment force for that wrapped load. The display device 42 and/or control system 36 can be configured such that, if the value of the containment force for the areas 59 is below (fails to meet) a predetermined minimum required containment force standard for that particular type of load, those areas 59 are displayed in a color that readily indicates that those areas 59 fall below the standard so that a machine operator can take corrective action. For example, the areas 59 can be displayed in red. This data can be stored in the control system 36 along with the associated date of the data, the associated roll of packaging film used, and/or the associated load wrapped, for later recall and consideration when, for example, a problem was reported with shipped loads.

The display device 42 and/or control system 36 can be configured to indicate the numerical value of the areas 59, as well as the numerical value of the predetermined minimum required containment force standard for that particular type of load. In the illustrated example, the predetermined minimum required containment force standard is 5 pounds, and the minimum containment force 59 for the particular wrapped load is 1 pound and 9 ounces. The display device 42 and/or control system 36 can be configured such that, since the minimum containment force is below (fails to meet) the predetermined minimum required containment force standard, the numerical value of the minimum containment force and/or its display heading "Min Containment Force" (or similar) are displayed in a color that readily indicates that fact so that a machine operator can take corrective action. For example, the numerical value of the minimum containment force and/or its display heading "Min Containment Force" (or similar) can be displayed in red. The display device 42 can also be configured to indicate the variance between the sensed containment force and the minimum required containment force, similarly color coded to indicate acceptability or unacceptability. This data can be stored in the control system 36 along with the associated date of the data, the associated roll of packaging film used, and/or the associated load wrapped, for later recall and consideration when, for example, a problem was reported with shipped loads.

The wrap profile data 60, which can be in the form of a vertical bar graph, is the number of film breaks per roll of film or per wrapped load as sensed by the control system 36. The vertical axis of the bar graph 60, on one side, is graduated in increments of number of film breaks, for example one (1) film break through five (5) film breaks. The value of acceptable film breaks per roll of film or per wrapped load is indicated on the other side of the bar graph 60 at 62. In the illustrated example, the standard 62 is 1 (one) film break per roll, and the number film breaks sensed 64 is about three (3). The display device 42 and/or control system 36 can be configured such that, since the number of film breaks is greater than the predetermined film breaks standard (fails to meet the film breaks standard), the bar(s) or indicator(s) 64 of the bar graph is(are) displayed in a color that readily indicates that fact so that a machine operator can take corrective action. For example, the bar 64 can be displayed in red. The display device 42 can also be configured to indicate the variance between the number of sensed film breaks and the number of allowable film breaks, similarly color coded to indicate acceptability or unacceptability. This data can be stored in the control system 36 along with the associated date of the data, the associated roll of packaging film used, and/or the associated load wrapped, for later recall and consideration when, for example, a problem was reported with shipped loads.

Since the minimum containment force is below (does not meet) the containment force standard, and since the number of film breaks is above (does not meet) the film breaks standard, the wrapped load exhibiting the wrapping data displayed in FIG. 6 would be deemed risky to ship, i.e. the wrapping might fail during shipment.

Referring now to FIG. 7, the wrapping data for a load successfully wrapped and deemed safe to ship is illustrated. In the illustrated example, the areas 59 in the graph 58, being those areas in the load profile that exhibit the minimum or lowest containment force for that wrapped load, exceed the containment force standard for that particular type of load. The display device 42 and/or control system 36 can thus be configured to display those areas 59 in a color that readily indicates that those areas 59 exceed the standard. For example, the areas 59 can be displayed in green. In the illustrated example, the predetermined minimum containment force standard is 5 pounds, and the minimum containment force 59 for the particular wrapped load is 7 pounds and 1 ounce. The display device 42 and/or control system 36 can thus be configured to display the numerical value of the minimum containment force and/or its display heading "Min Containment Force" (or similar) in a color that readily indicates that it exceeds the standard. For example, the numerical value of the minimum containment force and/or its display heading "Min Containment Force" (or similar) can be displayed in green. In the illustrated example, the film breaks standard 52 is 1 (one) film break per roll, and the number of film breaks sensed 64 is less than one (1). The display device 42 and/or control system 36 can thus be configured to display the bar 64 of the bar graph in a color that readily indicates that the number of film breaks is less than the film break standard (meets the film break standard). For example, the bar 64 can be displayed in green. As discussed above in connection with FIG. 6, all of this data can be stored in the control system 36 along with the associated date of the data, the associated roll of packaging film used, and/or the associated load wrapped, for later recall and consideration when, for example, a problem was reported with shipped loads.

It is also contemplated that the control system 36 and/or display device 42 could provide additional or special signal functionality. For example, in the event that either or both of the minimum containment force indicators 59 and number of film breaks indicator 64 are displayed in red (or another color indicating that these standards have not been met), additional or special warnings may be displayed on the display device 42 and/or communicated to the machine operator or other personnel such as management. For example, these additional or special warnings could be in the form of an audible alarm, additional colored text or symbols, flashing text or symbols, and/or animations on the display device 42. Additionally or alternatively, an e-mail, text message, or other electronic communication may be sent to one or more remote electronic devices to alert the user or other personnel such as management.

Figure 8:
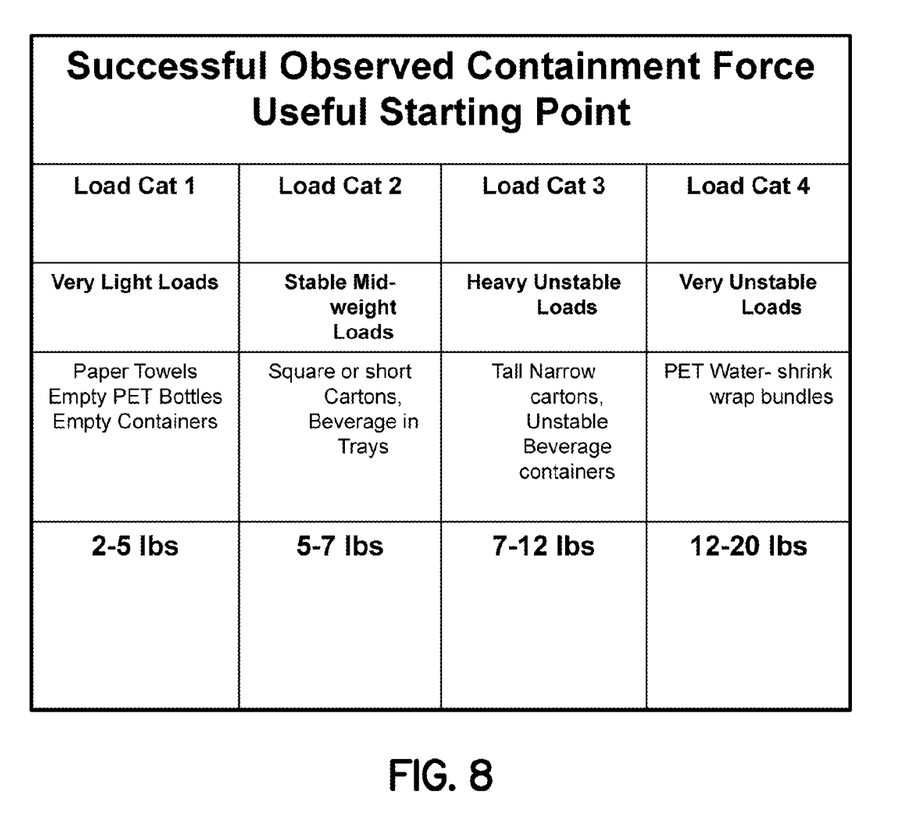
FIG. 8 is table of exemplary containment force values for various loads to be wrapped.

Referring now to FIG. 8, exemplary containment force standards for various categories of loads are illustrated. These predetermined values can be stored in the control system 36 for later recall to perform the display functions of FIGS. 6 and 7. For example, for a category 1 very light load, examples of which are paper towels, empty PET bottles, and empty containers, a suitable containment force standard is 2-5 pounds; for a category 2 stable mid-weight load, examples of which are square or short cartons and beverages in trays, a suitable containment force standard is 5-7 pounds; for a category 3 heavy unstable load, examples of which are tall narrow cartons, and unstable beverage containers, a suitable containment force standard is 7-12 pounds; and for a category 4 very unstable load, examples of which are PET water-shrink wrap bundles, a suitable containment force standard is 12-20 pounds.

A number of variables can be varied by a user of a wrapping machine to meet the film breaks standard and/or the containment force standard at the lowest film weight. Such variables include: top counts, bottom counts, wrap force payout percentage, prestretch percentage, total revolutions, film selected, film gauge, film width, overlap up, overlap down, and setting choices and settings.

Other embodiments of the invention will be apparent to those skilled in the art from consideration of the specification and practice of the invention disclosed herein. It is intended that the specification and examples be considered as exemplary only, with true scope and spirit of the invention being indicated by the following claims.

What is claimed is:

1. A method of generating data during wrapping of a load with a wrapping machine, the wrapping machine including a packaging material dispenser, the method comprising:
   determining with a sensing assembly a number of relative revolutions between the packaging material dispenser and the load during wrapping of the load and a height of the packaging material dispenser relative to the load during each relative revolution; and
   determining a number of layers applied to a face of the load at one or more heights based on an effective height of the packaging material as measured between first and second edges of the packaging material, the determined number of relative revolutions and the determined height of the packaging material dispenser, wherein the number of layers applied to the face of the load at the one or more heights is representative of a thickness of packaging material applied to the face of the load at the one or more heights.

2. The method of claim 1, further comprising displaying information associated with the determined number of layers on a display device.

3. The method of claim 2, wherein displaying information associated with the determined number of layers on the display device includes displaying a graph on the display device, the graph including a first axis indicative of height along a face of the load and a second axis indicative of the number of layers applied to the face of the load at the one or more heights.

4. The method of claim 1, further comprising determining a location on the face of the load having a least number of layers thereon.

5. The method of claim 4, further comprising determining a value indicative of a containment force exerted on the face of the load at the location on the face of the load with the least number of layers thereon.

6. The method of claim 5, further comprising displaying the determined value on a display device.

7. The method of claim 5, further comprising indicating when the determined value falls outside of a defined range.

8. The method of claim 1, further comprising determining a value indicative of a containment force exerted on the load by the applied layers based on the determined number of layers and a value indicative of an individual containment force exerted on the load by each layer.

9. The method of claim 8, further comprising determining the value indicative of the individual containment force exerted on the load by each layer by adjusting a baseline individual containment force value.

10. The method of claim 9, wherein adjusting the baseline individual containment force value includes adjusting the baseline individual containment force value based upon a length of packaging material dispensed during a relative revolution between the packaging material dispenser and the load.

11. The method of claim 9, wherein adjusting the baseline individual containment force value includes adjusting the baseline individual containment force value based upon a payout percentage used when wrapping the load.

12. The method of claim 9, further comprising:
initiating a wrap cycle to apply packaging material to a test load;
determining a number of layers applied to a face of the test load at one or more heights during the wrap cycle;
receiving entry of a containment force measurement taken from packaging material applied to the test load during the wrap cycle; and
determining the baseline individual containment force value from the determined number of layers applied to the face of the test load at the one or more heights during the wrap cycle and the received containment force measurement.

13. The method of claim 8, further comprising displaying information associated with the determined value indicative of the containment force on the display device.

14. The method of claim 13, wherein displaying the information includes indicating a height associated with a minimum containment force on the load.

15. The method of claim 13, wherein determining the value indicative of the containment force includes determining the value for a range of heights on the face of the load.

16. The method of claim 15, wherein displaying information associated with the determined value indicative of the containment force on the display device includes displaying a graph on the display device, the graph including a first axis indicative of height along a face of the load and a second axis indicative of the value indicative of the containment force.

17. The method of claim 16, wherein the graph includes one or more indicators along the first axis indicative of the containment force exerted on the load by the applied layers at the one or more heights.

18. The method of claim 17, wherein at least some of the indicators are displayed in a first color if above a predetermined value and are displayed in a second color if below the predetermined value.

19. The method of claim 17, further comprising displaying a numerical value corresponding to at least some of the indicators, wherein the numerical value is displayed in a first color if above a predetermined value and is displayed in a second color if below the predetermined value.

20. The method of claim 1, further comprising:
determining a number of film breaks occurring during wrapping of a plurality of loads, and
displaying information indicative of the determined number of film breaks on the display.

21. The method of claim 20, wherein displaying information indicative of the determined number of film breaks includes displaying a graph of the number of film breaks during wrapping of the plurality of loads load on the display device, the graph including an axis and one or more indicators along the axis indicative of the number of film breaks.

22. The method of claim 21, wherein the one or more indicators of the graph are displayed in different colors based upon whether the determined number of film breaks is above or below a predetermined film break value.

23. The method of claim 20, wherein displaying information indicative of the determined number of film breaks includes displaying a numerical value, wherein the numerical value is displayed in different colors based upon whether the determined number of film breaks is above or below a predetermined film break value.

24. A method of generating data during wrapping of a load with a wrapping machine, the wrapping machine including a packaging material dispenser, the method comprising:
determining a number of relative revolutions between the packaging material dispenser and the load during wrapping of the load with a sensing assembly on the wrapping machine;
determining a height of the packaging material dispenser relative to the load during each relative revolution;
determining a number of layers applied to a face of the load at one or more heights based on an effective height of the packaging material as measured between first and second edges of the packaging material, the determined number of relative revolutions and the determined height of the packaging material dispenser relative to the load during each relative revolution, wherein the number of layers applied to the face of the load at the one or more heights is representative of a thickness of packaging material applied to the face of the load at the one or more heights; and
displaying a graph on a display device, the graph including an axis indicative of the face of the load and one or more indicators along the axis indicative of the thickness of packaging material applied to the face of the load at the one or more heights.

25. The method of claim 24, further comprising indicating when the determined number of layers value falls outside of a defined range.

26. The method of claim 24, further including identifying a height range on the graph indicative of a least number of layers.

27. A method of generating data during wrapping of a load with a wrapping machine, the wrapping machine including a packaging material dispenser, the method comprising:
determining a number of relative revolutions between the packaging material dispenser and the load during wrapping of the load with a sensing assembly on the wrapping machine;
determining a height of the packaging material dispenser relative to the load during each relative revolution;
determining a value indicative of a containment force exerted on the load by packaging material applied to the load during wrapping at one or more heights based on the determined number of relative revolutions, the determined height of the packaging material dispenser relative to the load during each relative revolution, and a value indicative of an individual containment force exerted on the load by each layer of packaging material applied to the load; and
displaying a graph on a display device, the graph including an axis indicative of a face of the load and one or more indicators along the axis indicative of the containment force applied to the face of the load at the one or more heights.

28. The method of claim 27, further comprising determining a number of layers applied to the face of the load at the one or more heights based on the determined number of relative revolutions and the determined height of the packaging material dispenser relative to the load during each relative revolution, wherein the number of layers applied to the face of the load at the one or more heights is representative of a thickness of packaging material applied to the face of the load at the one or more heights.

29. The method of claim 27, further comprising displaying the determined value indicative of the containment force exerted on the load by packaging material applied to the load during wrapping at the one or more heights on the display device.

30. The method of claim 27, further comprising indicating when a determined value indicative of the containment force exerted on the load by packaging material applied to the load during wrapping at a first height among the one or more heights falls outside of a defined range.

31. A method for generating data during wrapping of a load with a wrapping machine, the method comprising:
storing a value for a characteristic associated with a packaging material by wrapping a test load with the packaging material and measuring the characteristic, wherein the characteristic is indicative of a containment force exerted on the test load by one layer of the packaging material;
sensing with a sensing assembly on the wrapping machine relative rotation between a packaging material dispenser and a second load different from the test load during wrapping of the second load;
determining at least one parameter associated with the packaging material dispensed to the wrapped second load based on the sensed relative rotation and the obtained value without removing the packaging material from the wrapped second load, wherein the at least one determined parameter includes a containment force exerted by the packaging material on the wrapped second load; and
displaying information associated with the at least one parameter on a display device.

32. The method of claim 31, further comprising:
measuring with a second sensing assembly on the wrapping machine a length of packaging material dispensed during wrapping of the second load;
obtaining a second value for a second characteristic that is indicative of a weight of the packaging material per unit of length, or a cost of the packaging material per unit length;
determining a second parameter associated with the packaging material dispensed to the wrapped second load based on the measured length and the obtained second value, wherein the determined second parameter includes a weight or a cost of the packaging material dispensed to the wrapped second load; and
displaying information associated with the second parameter on the display device.

33. The method of claim 32, further comprising displaying information associated with the measured length of packaging material dispensed.

34. The method of claim 31, further including indicating when the at least one parameter falls outside of a defined range.

35. The method of claim 31, wherein sensing relative rotation with the sensing assembly includes measuring a number of relative revolutions between the packaging material dispenser and the second load, wherein the at least one parameter is based on the measured number of relative rotations and the obtained value.

36. The method of claim 35, further comprising determining with a second sensing assembly on the wrapping machine a height of the packaging material relative to the second load during each relative revolution, wherein the at least one parameter is additionally based on the sensed height of the packaging material relative to the second load during at least one relative revolution.

37. The method of claim 36, further comprising determining a number of layers of packaging material applied at one or more heights on the second load based on the sensed height of the packaging material relative to the second load during each relative revolution, wherein the number of layers applied to the face of the load at the one or more heights is representative of a thickness of packaging material applied to the load at the one or more heights.

38. A method of generating data during wrapping of a load with a wrapping machine, the wrapping machine including a packaging material dispenser, the method comprising:
determining with a sensing assembly a number of relative revolutions between the packaging material dispenser and the load during wrapping of the load and a height of the packaging material dispenser relative to the load during each relative revolution;
determining a value indicative of a containment force exerted on the load by packaging material applied to the load during wrapping at one or more heights based on the determined number of relative revolutions, the determined height of the packaging material dispenser relative to the load during each relative revolution, and a value indicative of an individual containment force exerted on the load by each layer of packaging material applied to the load;
determining based upon the value whether the load meets a predetermined minimum required containment force standard for the load; and
displaying information on a display device indicating whether the load meets the predetermined minimum required containment force standard for the load.

39. The method of claim 38, further comprising determining a number of layers applied to a face of the load at the one or more heights based on the determined number of relative revolutions and height, wherein the number of layers applied to the face of the load at the one or more heights is representative of a thickness of packaging material applied to the face of the load at the one or more heights, and wherein determining the value indicative of the containment force exerted on the load is based on the determined number of layers.

40. The method of claim 38, wherein determining whether the load meets the predetermined minimum required containment force standard for the load includes determining whether the value meets the predetermined minimum required containment force standard at any height among the one or more heights.

41. The method of claim 40, wherein displaying the information includes displaying a wrap profile for the load and indicating one or more areas of the wrap profile corresponding to any height among the one or more heights for which the value fails to meet the predetermined minimum required containment force standard.

42. The method of claim 38, wherein displaying the information includes displaying a numerical value corresponding to a minimum containment force for the load.

43. The method of claim 42, wherein displaying the information includes displaying the numerical value in different colors based upon whether the load meets the predetermined minimum required containment force standard for the load.

44. The method of claim 38, further comprising, in response to determining that the load fails to meet the predetermined minimum required containment force standard for the load, generating an audible or graphical warning.

45. The method of claim 38, further comprising, in response to determining that the load fails to meet the predetermined minimum required containment force standard for the load, sending an electronic communication to a remote electronic device.

46. The method of claim 38, wherein the predetermined minimum required containment force standard is selected from among a plurality of containment force standards respectively associated with a plurality of categories of loads.

47. The method of claim 46, wherein the plurality of categories of loads includes a very light load, a stable mid-weight load, a heavy unstable load, and a very unstable load.

* * * * *